(12) United States Patent
Dos Santos et al.

(10) Patent No.: US 11,667,593 B2
(45) Date of Patent: Jun. 6, 2023

(54) COMPOUNDS, INCLUDING NONSYMMETRICAL POLYAROMATIC HYDROCARBONS, AND METHODS

(71) Applicant: The Florida State University Research Foundation, Inc., Tallahassee, FL (US)

(72) Inventors: Nikolas Ramos Dos Santos, Tallahassee, FL (US); Igor Alabugin, Tallahassee, FL (US); Alexandria Palazzo, Tallahassee, FL (US)

(73) Assignee: The Florida State University Research Foundation, Inc., Tallahassee, FL (US)

( * ) Notice: Subject to any disclaimer, the term of this patent is extended or adjusted under 35 U.S.C. 154(b) by 0 days.

(21) Appl. No.: 17/903,529

(22) Filed: Sep. 6, 2022

(65) Prior Publication Data
US 2023/0106858 A1    Apr. 6, 2023

Related U.S. Application Data

(60) Provisional application No. 63/252,005, filed on Oct. 4, 2021.

(51) Int. Cl.
| | | |
|---|---|---|
| *C07C 5/393* | (2006.01) | |
| *C07C 15/38* | (2006.01) | |
| *C07C 6/04* | (2006.01) | |

(52) U.S. Cl.
CPC ............ *C07C 6/04* (2013.01); *C07C 5/393* (2013.01); *C07C 15/38* (2013.01); *C07C 2603/50* (2017.05)

(58) Field of Classification Search
CPC ............ C07C 6/04; C07C 5/393; C07C 15/38; C07C 2603/50
See application file for complete search history.

(56) References Cited

PUBLICATIONS

Feng et al. ("Synthesis and photophysical properties of novel butterfly-shaped blue emitters based on pyrene." Org. Biomol. Chem., 2013, 11, 8366-8374) (Year: 2013).*
E. Gonzalez-Rodriguez, et al. J. Am. Chem. Soc. 2020, 142, 18, 8352-8366.
D. B. Walker, et al. Synthesis 2010, 21, 3686-3692.
R. K. Kawade et al. Phenalenannulations: Three-Point Double Annulation Reactions that Convert Benzenes into Pyrenes, Jun. 3, 2020.
N. H. Laarhoven, et al. Photodehydrocyclizations in Stilbene-Like Compounds-II, Tetrahedron. vol. 26, 169-1083, 1970.

* cited by examiner

*Primary Examiner* — In Suk C Bullock
*Assistant Examiner* — Jason Y Chong
(74) *Attorney, Agent, or Firm* — Eversheds Sutherland (US) LLP (57) ABSTRACT

Methods of forming arenes, including asymmetrical arenes, such as asymmetrical pyrene derivatives. Substituents of starting materials may be selected to direct a photochemical cascade and possibly a 1,2-aryl shift. The methods may include a Mallory cyclization, which is controlled, at least in part, by substituents of the starting materials. Compounds and compositions including asymmetrical arenes.

20 Claims, 4 Drawing Sheets

COMPOUNDS, INCLUDING NONSYMMETRICAL POLYAROMATIC HYDROCARBONS, AND METHODS

CROSS-REFERENCE TO RELATED APPLICATIONS

This application claims priority to U.S. Provisional Patent Application No. 63/252,005, filed Oct. 4, 2021, which is incorporated by reference herein.

STATEMENT REGARDING FEDERALLY SPONSORED RESEARCH OR DEVELOPMENT

This invention was made with government support under Contract Nos. CHE-1800329 and CHE-2102579 awarded by The National Science Foundation. The government has certain rights in this invention.

BACKGROUND

Polyaromatic hydrocarbons (PAHs), such as pyrene and its derivatives, have uses in a number of industries and products, including organic electronic devices, due to their high fluorescence quantum yields and inherent deep-blue emission.

Pyrene is an important molecular core for organic electronics, where it has known uses in field-effect transistors (see, e.g., S. Diring, et al. J. Am. Chem. Soc., 2009, 131, 18177-1), OLEDs (organic light emitting diodes) (see, e.g., J. Wu, et al. Chem. Rev., 2007, 107, 718-747), and OFETs (organic field effect transistors) (see, e.g., W. L. Jia, et al. J. Mater. Chem., 2004, 14, 3344-3350). The useful characteristics of pyrene chromophores may include their inherent deep blue emission, long-lived singlet excited states, high fluorescence quantum yields, excimer formation in solution, and/or color-changing aggregation in the solid state. However, the methods for synthesizing pyrene with diverse substitution patterns are scarce. The few available methods rely on two main strategies.

The first strategy is to functionalize an existing pyrene core. The second approach is to introduce substituents into a starting material that is converted into a pyrene core.

Direct methods focus on two main areas in the pyrene core: the 1,2,3,5,6,7 positions (non-K region) and the 4,5,9,10 positions (the K region). The latter positions can be more difficult to functionalize. The non-K region of pyrene typically is most activated for electrophilic aromatic substitution at the 1, 3, 6, and 8 positions (see, e.g., L. Altschuler, et al. J. Am. Chem. Soc. 1966, 88, 5837; and M. J. S. Dewar, et al. J. Am. Chem. Soc. 1989, 111, 3804). However, the 2 and 7 positions can be substituted selectively by the use of bulky electrophiles (see, e.g., D. N. Coventry, et al. Chem. Commun., 2005, 2172-2174; A. Miyazawa, et al. Chem. Express 1990, 5, 381), and transition metals may be used to assist the reaction. These methods typically fail when selective di- and tri-substitution of the pyrene core is needed.

While mono-substitution of the non-K region usually can be controlled, further substitution of the pyrene core often leads to a statistical distribution of regioisomers from all reactive positions. So, although there are many methods to substitute pyrene, direct methods often lead only to mono-substituted or tetra substituted pyrenes which are symmetrical (see, e.g., T. M. Figueira-Duarte et al. Chem. Rev., 2011, 111, 7260-7314). Accordingly, non-symmetrical pyrenes have been mostly unexplored.

As a result, methods for synthesizing non-symmetrical pyrenes are needed to facilitate the growth of the understanding and availability of pyrene-based materials.

It has been shown that the 2 position of pyrene can be selectively substituted in great yields using an iridium catalyst. A common precursor to tetrafunctional pyrenes is 1,3,6,8-tetrabromopyrene which can be synthesized in 90% yield by the reaction with $Br_2$ in nitrobenzene at 160° C. (see, e.g., S. Bernhardt, et al. Chem.—Eur. J. 2006, 12, 6117). Converting pyrene into di-substituted pyrenes via electrophilic aromatic substitution leads to mixtures of 1,6- and 1,8-substituted pyrenes that can be difficult to separate (see, e.g., J. Grimshaw, et al. Chem. Soc. Perkin Trans. 1 1972, 1622).

Methods for the substitution of the K-region of pyrene are even more scarce. These methods can include using two tert-butyl groups at the 2,7-positions as protecting groups with the assistance of an iron catalyst (see, e.g., T. Yamato, et al. Chem. Soc. Perkin Trans. 1 1997, 1201), direct nitration of pyrene, as well as indirect approaches, such as the HHpy (hexahydropyrene) approach, which employs reducing pyrene into 1,2,3,6,7,8-hexahydropyrene followed by subsequent electrophilic aromatic substitution to the K-region, and a re-aromatization step after substitution (see, e.g., A. Streitwieser Jr., et al. J. Org. Chem., 1965, 30, 1470-1473).

The second group of pyrene syntheses relies on strategies to construct the substituted pyrene core via cycle-forming reactions. These methods rely on two main strategies. The first strategy is to use transannular ring closure (TRC) of [2,2]metacyclophanes to first produce a THpy (tetrahydropyrene) intermediate, which, upon further oxidation, can be converted into pyrene (see, e.g., J. M. Casas-Solvas, et al. Org. Biomol. Chem., 2014, 12, 212). An electrophile can be used to activate the transannular ring closure, forming THpy—this electrophile can be incorporated into the product (see, e.g., F. Vögtle et al. Angew. Chem., Int. Ed. Engl., 1972, 11, 73-158). The other is the employment of different biphenyl annulations. These reactions include the photocyclization of 2,2'-divinyl biphenyls, which proceeds through two separate biphenyl cyclizations to give a THpy structure, which can then be separately re-aromatized in a separate operation (see, e.g., W. H. Laarhoven et al. J. Chem. Soc., Perkin Trans. 1, 1972, 2074-2079), a sulfur intermediate expulsion from ortho-thiocarbonyl substituted biphenyl based polymeric ketones (see, e.g., Z. Y. Wang et al. Macromolecules, 1992, 25, 5851-5854), and the cyclization of o,o'-dialkynyl substituted biphenyls (see, e.g., D. B. Walker, et al. Synthesis, 2010, 3686-3692). Recent processes have used 1,4-substituted naphthalenes to make pyrene using $Bu_3SnH$ through a radical annulation mechanism (see, e.g., E. Gonzalez-Rodriguez, et al. J. Am. Chem. Soc. 2020, 142, 18, 8352-8366), or are based on Fürstner's phenanthrene synthesis (see, e.g., D. B. Walker, et al. Synthesis 2010, 21, 3686-3692).

Although the known examples of this approach are scarce, this group of transformations can lead to efficient bottom-up strategies for the synthesis of substituted pyrenes. An important drawback of the current methods is the lack of direct strategies for the synthesis of non-symmetrical pyrenes.

Another de-novo construction of substituted pyrene core is provided by Kawade et al. (R. K. Kawade, et al. Angew. Chem. Int. Ed. 2020, 59, 14352-14357). Although this strategy reliably yields pyrene products in moderate yields 48-64%, it requires a complex synthesis of a starting precursor. The latter must undergo the Wittig reaction to form a radical precursor, which then must be subjected to a complex three-part procedure to yield pyrene products.

There remains a need for new and/or improved synthetic strategies for preparing PAHs, including nonsymmetrical PAHs, including methods that may allow for selective functionalization of a pyrene core and/or modular control of its physical properties.

BRIEF SUMMARY

Provided herein are methods that permit, in some embodiments, the preparation of previously unavailable nonsymmetrical arenes, such as pyrenes, from bis-stilbenes or other starting materials. In some embodiments, the methods provided herein are directed to a new strategy for the synthesis of unsymmetrical pyrenes and higher order PAHs via a one-pot double photocyclization sequence of simple and readily available starting materials.

In one aspect, methods of forming arenes are provided, including asymmetrical arenes, such as asymmetrical pyrenes. In some embodiments, the methods include providing a compound of formula (Ia), a compound of formula (Ib), or a combination thereof— wherein each R is independently selected from the group consisting of a $C_1$-$C_{20}$ alkyl and a $C_1$-$C_{20}$ aryl, and each R' is independently selected from the group consisting of hydrogen, a $C_1$-$C_{20}$ alkyl, a $C_1$-$C_{20}$ aryl, a $C_1$-$C_{20}$ alkoxy, and a $C_1$-$C_{20}$ aryloxy; irradiating the compound of formula (Ia), the compound of formula (Ib), or the combination thereof, optionally in the presence of an oxidant, to form a compound of formula (II)— and irradiating the compound of formula (II) to form a compound of formula (IIIa), a compound of formula (IIIb), or a combination thereof—

In another aspect, compounds are provided, including arenes, such as asymmetrical arenes. In some embodiments, the compounds are of formula (IIIa) or formula (IIIb):

wherein each R is independently selected from the group consisting of a $C_1$-$C_{20}$ alkyl and a $C_1$-$C_{20}$ aryl, and each R' is independently selected from the group consisting of hydrogen, a $C_1$-$C_{20}$ alkyl, a $C_1$-$C_{20}$ aryl, a $C_1$-$C_{20}$ alkoxy, and a $C_1$-$C_{20}$ aryloxy. Compositions include a compound of formula (IIIa) and a compound of formula (IIIb) also are provided.

Additional aspects will be set forth in part in the description which follows, and in part will be obvious from the description, or may be learned by practice of the aspects described herein. The advantages described herein may be realized and attained by means of the elements and combinations particularly pointed out in the appended claims. It is to be understood that both the foregoing general description

DETAILED DESCRIPTION

Embodiments of the methods provided herein are based on a novel cascade that can couple stilbene photocyclization (e.g., Mallory reaction) with a new photocyclization at the bay region of phenanthrene. In order to avoid a second Mallory reaction in favor of a preferred reaction, blocking groups, which are the "R" groups in the structures described herein, may be applied at a core benzene ring of embodiments of the di-stilbene reactants. Not wishing to be bound by any particular theory, it is believed that embodiments of the methods provided herein can (i) rely on starting materials that can be relatively easily synthesized from commercially available substrates, and/or (ii) control the direction of cyclization to yield a desired product selectively.

In some embodiments, the compounds, including pyrenes, provided herein include a non-symmetrical substitution pattern, which can affect the compounds' electronic properties and/or solid state packing. The structures of the compounds may be tunable, for example, via precursor selection, which may be simple molecules that can be assembled in a modular way in a controlled and/or regioselective matter. Not wishing to be bound by any particular theory, it is believed that photochemical activation can be beneficial, at least in some embodiments, because it may allow a synthetic procedure to start with E-alkenes, Z-alkenes, or a mixture of E- and Z-alkenes as the reactants, as these geometric isomers can readily interconvert under photochemical conditions.

Methods

Provided herein are methods of forming arenes, including nonsymmetrical pyrene derivatives. In some embodiments, the methods include providing a compound of formula (Ia), a compound of formula (Ib), or a combination thereof— formula (Ia)

formula (Ib)

wherein each R is independently selected from the group consisting of a $C_1$-$C_{20}$ alkyl and a $C_1$-$C_{20}$ aryl, and each R' is independently selected from the group consisting of hydrogen, a $C_1$-$C_{20}$ alkyl, a $C_1$-$C_{20}$ aryl, a $C_1$-$C_{20}$ alkoxy, and a $C_1$-$C_{20}$ aryloxy. In some embodiments, the methods include providing only a compound of formula (Ia), and not a compound of formula (Ib).

Each R and each R' are selected independently of each other, and any two of the four substituents (R, R, R', R') of formulas (Ia) and (Ib) may be the same or different; therefore, for example, when an R and an R' are selected from "a $C_1$-$C_{20}$ alkyl", the same or different $C_1$-$C_{20}$ alkyls may be selected for the R and the R'; and, as a further example, when a first R and a second R are independently selected from a "$C_1$-$C_{20}$ aryl", the same or different $C_1$-$C_{20}$ aryls may be selected for the first R and the second R.

In some embodiments, each R is independently selected from a $C_1$-$C_{15}$ alkyl, a $C_1$-$C_{10}$ alkyl, a $C_1$-$C_5$ alkyl, $C_1$-$C_4$ alkyl, or a $C_1$-$C_3$ alkyl. In some embodiments, each R is methyl.

In some embodiments, each R' is independently selected from a $C_1$-$C_{15}$ alkoxy, a $C_1$-$C_{10}$ alkoxy, or a $C_1$-$C_5$ alkoxy. In some embodiments, each R' is methoxy (—OMe). In some embodiments, each R' is independently selected from a $C_1$-$C_{15}$ alkyl, $C_1$-$C_{10}$ alkyl, or $C_1$-$C_5$ alkyl. In some embodiments, each R' is methyl. In some embodiments, each R' is hydrogen.

In some embodiments, the methods include irradiating the compound of formula (Ia), the compound of formula (Ib), or the combination thereof to form a compound of formula (II)— formula (II)

and irradiating the compound of formula (II) to form a compound of formula (IIIa), a compound of formula (IIIb), or a combination thereof— formula (IIIa)

formula (IIIb)

The compound of formula (II) may or may not be isolated prior to being irradiated. Therefore, a compound of formula (II) may be an intermediate product that is not isolated in some embodiments of the methods described herein. When a compound of formula (II) is not isolated, irradiation may be continuously or intermittently applied until one or more desired products are formed, such as a compound of formula (IIIa) and/or formula (IIIb).

The "irradiating" may be performed continuously or intermittently with electromagnetic radiation of any one or more wavelengths effective to produce the products described herein. For example, ultraviolet (UV) irradiation may be used. In some embodiments, the UV irradiation has one or more wavelengths of about 10 nm to about 400 nm, about 100 nm to about 400 nm, about 200 nm to about 400 nm, or about 300 nm to about 400 nm. The "irradiating" may occur for a time effective to facilitate a reaction to a desired degree.

The "irradiating" provided herein may be performed in the presence of an oxidant, in an atmosphere that includes 02, or a combination thereof. The oxidants used in the various "irradiating" steps described herein may be the same or different. In some embodiments, (i) the irradiating of the compound of formula (Ia), the compound of formula (Ib), or the combination thereof occurs in the presence of a first oxidant, and/or (ii) the irradiating of the compound of formula (II) occurs in the presence of a second oxidant; and the first oxidant and the second oxidant may be the same or different. In some embodiments, the first oxidant, the second oxidant, or both the first oxidant and the second oxidant includes iodine or a compound containing one or more iodine atoms. Any oxidant(s) known in the art may be used, however (see, e.g., Laarhoven W. H. *Org. Photochem.* 1989; 10:163-308). In some embodiments, iodine is used in combination with propylene oxide or other scavenger.

A compound of formula (Ia) and/or a compound of formula (Ib) may be obtained by any methods known in the art.

In some embodiments, the providing of the compound of formula (Ia), the compound of formula (Ib), or the combination thereof includes providing a compound of formula (A)— formula (A)

wherein X is a halogen; providing a compound of formula (B)— formula (B)

and contacting the compound of formula (A) and the compound of formula (B) to form the compound of formula (Ia), the compound of formula (Ib), of a combination thereof. X may be any halogen, such as chlorine or bromine.

The contacting of a compound of formula (A) and a compound of formula (B) may occur in the presence of a base, a catalyst, or a combination thereof. The catalyst may include a palladium catalyst (e.g., Pd(OAc)$_2$), such as those commonly used in the "Heck" reaction (see, e.g., Heck, R. F. Org. React. 1982, 27, 345-390). The base may include an amine, such as a tertiary amine (see Examples).

As described herein, the selection of R and/or R' may determine a product formed by the methods described herein. In some embodiments, each R' is a C$_1$-C$_{20}$ alkyl, such as methyl, and the irradiating of the compound of formula (II) converts about 90% to about 99%, about 90% to 100%, at least 90%, at least 95%, at least 99%, or 100%, by mole, of the compound of formula (II) to the compound of formula (IIIa). In other words, if a reaction produces 0.5 moles of formula (II), then 0.45 moles (90%) to 0.5 moles (100%) of the compound of formula (II) is converted to the compound of formula (IIIa). In some embodiments, R' is a C$_1$-C$_{20}$ alkoxy, such as methoxy, and the irradiating of the compound of formula (II) converts about 90% to about 99%, about 90% to 100%, at least 90%, at least 95%, at least 99%, or 100%, by mole, of the compound of formula (II) to the compound of formula (IIIb).

Compounds

Also provided herein are compounds and compositions. In some embodiments, the compounds are of formula (IIIa) or formula (IIIb).

formula (IIIa)

-continued formula (IIIb)

wherein R is selected from the group consisting of a $C_1$-$C_{20}$ alkyl and a $C_1$-$C_{20}$ aryl, and R' is selected from the group consisting of hydrogen, a $C_1$-$C_{20}$ alkyl, a $C_1$-$C_{20}$ aryl, a $C_1$-$C_{20}$ alkoxy, and a $C_1$-$C_{20}$ aryloxy. Also provided are compositions that include a compound of formula (IIIa) and a compound of formula (IIIb).

The formulas herein, including formula (Ia), formula (Ib), formula (II), formula (IIIa), and formula (IIIb), read on compounds having the structures as drawn, tautomers thereof, and combinations thereof.

The phrases "$C_1$-$C_{20}$ alkyl", a "$C_1$-$C_{20}$ aryl", a "$C_1$-$C_{20}$ alkoxy", "$C_1$-$C_{20}$ aryloxy", and the like, as used herein, generally refer to alkyl, aryl, alkoxy, and aryloxy groups, respectively, containing 1 to 20 carbon atoms. Examples of alkyl groups, in each instance, include, but are not limited to, an alkyl group, a cycloalkyl group, an alkenyl group, a cycloalkenyl group, an alkynyl group, an alkadienyl group, a cyclic group, and the like, and includes all substituted, unsubstituted, branched, and linear analogs or derivatives thereof, in each instance having 1 to about 20 carbon atoms. Examples of alkyl groups include, but are not limited to, methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl and dodecyl. Cycloalkyl moieties may be monocyclic or multicyclic, and examples include cyclopropyl, cyclobutyl, cyclopentyl, cyclohexyl, and adamantyl. Additional examples of alkyl moieties have linear, branched and/or cyclic portions (e.g., 1-ethyl-4-methyl-cyclohexyl). Representative alkenyl moieties include vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl and 3-decenyl. Representative alkynyl moieties include acetylenyl, propynyl, 1-butynyl, 2-butynyl, 1-pentynyl, 2-pentynyl, 3-methyl-1-butynyl, 4-pentynyl, 1-hexynyl, 2-hexynyl, 5-hexynyl, 1-heptynyl, 2-heptynyl, 6-heptynyl, 1-octynyl, 2-octynyl, 7-octynyl, 1-nonynyl, 2-nonynyl, 8-nonynyl, 1-decynyl, 2-decynyl and 9-decynyl. Examples of aryl moieties include, but are not limited to, anthracenyl, azulenyl, biphenyl, fluorenyl, indan, indenyl, naphthyl, phenanthrenyl, phenyl, 1,2,3,4-tetrahydro-naphthalene, tolyl, xylyl, mesityl, benzyl, and the like, including any heteroatom substituted derivative thereof. Therefore, the term "aryl", as used herein, including arylalkyl groups, such as benzyl.

As used herein, the term "alkoxy" and "aryloxy" refer to substituents having the structures "—O-alkyl" and "—O-aryl", respectively; therefore, the alkoxy and aryloxy groups may include any of the foregoing alkyl and aryl groups, respectively.

Unless otherwise indicated, the term "substituted," when used to describe a chemical structure or moiety, refers to a derivative of that structure or moiety wherein (i) a multivalent non-carbon atom (e.g., oxygen, nitrogen, sulfur, phosphorus, etc.) is bonded to one or more carbon atoms of the chemical structure or moiety (e.g., a "substituted" $C_4$ alkyl may include, but is not limited to, diethyl ether moiety, a methyl propionate moiety, an N,N-dimethylacetamide moiety, etc., and a "substituted" $C_{12}$ aryl may include, but is not limited to, an oxydibenzene moiety, a benzophenone moiety, etc.) or (ii) one or more of its hydrogen atoms (e.g., chlorobenzene may be characterized generally as a $C_6$ aryl "substituted" with a chlorine atom) is substituted with a chemical moiety or functional group such as alcohol, alkoxy, alkanoyloxy, alkoxycarbonyl, alkenyl, alkyl (e.g., methyl, ethyl, propyl, t-butyl), alkynyl, alkylcarbonyloxy (—OC(O) alkyl), amide (—C(O)NH-alkyl- or -alkylNHC(O)alkyl), tertiary amine (such as alkylamino, arylamino, arylalkylamino), aryl, aryloxy, azo, carbamoyl (—NHC(O)O-alkyl- or —OC(O)NH-alkyl), carbamyl (e.g., $CONH_2$, as well as CONH-alkyl, CONH-aryl, and CONH-arylalkyl), carboxyl, carboxylic acid, cyano, ester, ether (e.g., methoxy, ethoxy), halo, haloalkyl (e.g., —$CCl_3$, —$CF_3$, —$C(CF_3)_3$), heteroalkyl, isocyanate, isothiocyanate, nitrile, nitro, oxo, phosphodiester, sulfide, sulfonamido (e.g., $SO_2NH_2$), sulfone, sulfonyl (including alkylsulfonyl, arylsulfonyl and arylalkylsulfonyl), sulfoxide, thiol (e.g., sulfhydryl, thioether) or urea (—NHCONH-alkyl-).

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

While certain aspects of conventional technologies have been discussed to facilitate disclosure of various embodiments, applicants in no way disclaim these technical aspects, and it is contemplated that the present disclosure may encompass one or more of the conventional technical aspects discussed herein.

The present disclosure may address one or more of the problems and deficiencies of known methods and processes. However, it is contemplated that various embodiments may prove useful in addressing other problems and deficiencies in a number of technical areas. Therefore, the present disclosure should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

In the descriptions provided herein, the terms "includes," "is," "containing," "having," and "comprises" are used in an open-ended fashion, and thus should be interpreted to mean "including, but not limited to." When materials or methods are claimed or described in terms of "comprising" various steps or components, the materials or methods can also "consist essentially of" or "consist of" the various steps or components, unless stated otherwise.

The terms "a," "an," and "the" are intended to include plural alternatives, e.g., at least one. For instance, the disclosure of "a compound of formula (Ia)", "an oxidant", and the like, is meant to encompass one, or mixtures or combinations of more than one compound of formula (Ia), oxidant, and the like, unless otherwise specified.

Various numerical ranges may be disclosed herein. When Applicant discloses or claims a range of any type, Applicant's intent is to disclose or claim individually each possible number that such a range could reasonably encompass, including end points of the range as well as any sub-ranges and combinations of sub-ranges encompassed therein, unless otherwise specified.

Moreover, all numerical end points of ranges disclosed herein are approximate. As a representative example, Applicant discloses, in some embodiments, that the irradiating of the compound of formula (II) converts about 90% to about 99%, by mole, of the compound of formula (II) to the compound of formula (IIIa). This range should be interpreted as encompassing about 90% and about 99%, and further encompasses "about" each of 91%, 92%, 93%, 94%, 95%, 96%, 97%, and 98%, including any ranges and sub-ranges between any of these values.

As used herein, the term "about" means plus or minus 10% of the numerical value of the number with which it is being used.

EXAMPLES

The present invention is further illustrated by the following examples, which are not to be construed in any way as imposing limitations upon the scope thereof. On the contrary, it is to be clearly understood that resort may be had to various other aspects, embodiments, modifications, and equivalents thereof which, after reading the description herein, may suggest themselves to one of ordinary skill in the art without departing from the spirit of the present invention or the scope of the appended claims. Thus, other aspects of this invention will be apparent to those skilled in the art from consideration of the specification and practice of the invention disclosed herein.

Example 1 Synthesis of Non-Symmetrical Tetra-Substituted Pyrenes

In this example, a test was conducted to determine whether the readily available meta-bis-styrylbenzenes (Scheme 1) would yield pyrene product in a one-pot photochemical transformation.

Scheme 1. De-Novo photochemical synthesis of non-symmetric tetra-substituted pyrenes.

"Blocking Groups"
(e.g., alkyl, aryl)

The reactants of this example were prepared expediently using a double Heck reaction of styrenes with commercially available 1,5-dibromo-2,4-dialkylbenzenes. In order to ensure the photocyclization selectivity and to disfavor the Mallory reaction at the second step of the cascade, robust blocking groups, i.e., "R" substituents, were used.

The photocyclization of stilbenes was catalyzed by the addition of iodine in the presence of $O_2$ (see, e.g., F. B. Mallory, et al. J. Am. Chem. Soc. 1964, 86, 3094-3102; and C. S. Wood, et al. J. Org. Chem. 1964, 29, 11, 3373-3377). It was believed that light cleaved $I_2$ into radicals that then participated in a chain reaction to form the oxidized product and HI.

Under some conditions (cat. $I_2$, air, and light), different mixtures of cis- and trans-stilbenes produced identical products due to rapid photo-isomerization. Therefore, it was possible to use mixtures of cis- and trans-isomers as one starting material even though it was believed that only the cis isomer was capable of the cyclization.

Although iodine was the oxidant used in the reactions of this example, the use of other oxidants is envisioned. Iodine also has been used to control product selectivity by attacking the C—H bond and preventing elimination of methanol via the C—OMe bond scission in a OMe-substituted stilbene. However, it should be noted that excess $I_2$ can lower reaction yields through undesirable side reactions with the HI byproduct (see, e.g., K. Noller, et al. Chem. Ber. 1988, 121, 1609-1616).

Conditions were used for the Mallory reaction that were designed to prevent undesirable side reactions with HI (see, e.g., L. Liu, et al. J. Org. Chem. 1991, 56, 3769-3775; and A. Sudhakar, et al. Tetrahedron Lett. 1986, 27, 2231-2234). For example, methyloxirane was employed as an HI scavenger. Because of this modification, the reactions of this example may not have been catalytic in iodine anymore, and equimolar amounts of $I_2$ were necessary to complete the transformation. This method, however, can lead to cleaner reactions and better yields of the photocyclization.

In this example, the following strategy was used to synthesize non-symmetric pyrenes in good yields by assembling the pyrene core via two photocyclizations. This example used stilbene photocyclization and a novel photocyclization at the bay region of phenanthrene (Scheme 2, bottom right).

The formation of the usual products was avoided by applying the following strategy, which included using blocking groups that allowed the double photocyclization to be redirected exclusively to the formation of the products depicted at Scheme 2. This design resulted in a simpler and much more convenient synthesis of pyrenes than other known methods.

The strategy of this example directed the double cyclization shown at Scheme 2 towards the selective formation of the depicted product through the use of different blocking groups at the positions that were involved in the formation of undesired products 1 and 2:

This example tested whether methyl (Me) or methoxy (OMe) groups could serve as useful and/or effective blocking substituents.

It was determined that when each R was methoxy, these blocking groups produced a sole product of two Mallory cyclizations, as depicted at the bottom left of Scheme 2. The identity of this product was unambiguously confirmed with X-ray crystallography (FIG. 1C). Since methoxy blocking groups did not work as expected in the method of this example, more robust methyl blocking groups were used at the R position in this example.

This approached permitted the required meta-bis-styrene substituted arenes to be formed in one step with the Heck reaction of commercially available 1,5-dibromo-2,4-dialkyl-benzenes and commercially available styrenes. It was found that such reactions proceeded with 10 mol % of $Pd(OAc)_2$, 4 equivalents of triethylamine and 30% triphenylphosphine dissolved in acetonitrile at 100° C. over-night to provide the required bis-stilbenes in 70-80% yields.

The methyl-substituted precursors readily formed the expected tetrasubstituted nonsymmetrical pyrenes upon irradiation in the presence of $I_2$ and methyloxirane. For such reactions, the formation of the tetra-substituted non-symmetrical pyrene was observed in 55% yield for R'=R=Me.

Also observed was a second product formed via two Mallory photocyclizations, unexpectedly eliminating a Me blocking group in the process. The two products were formed in a 5:2 ratio. This was believed to be an important result because it illustrated that the blocking groups were indeed capable of preventing the $2^{nd}$ Mallory cyclization and redirecting the photochemical cascade toward the formation of pyrene product (Scheme 2).

Scheme 2. The photochemical double cyclization cascade that allows a two-step transformation of 1,3-dihalobenzenes to phenanthrenes.

R' = alkyl

R' = OMe
1,2-Ar shift

Photocascades

Unprecedently, the photochemical cascade of substrates with the Me-blocking groups proceeded even further via a formal 1,2-aryl group shift when a new remote substituent, R'=OMe, was introduced. The new product is depicted at the bottom right of Scheme 2.

Figure 1A:
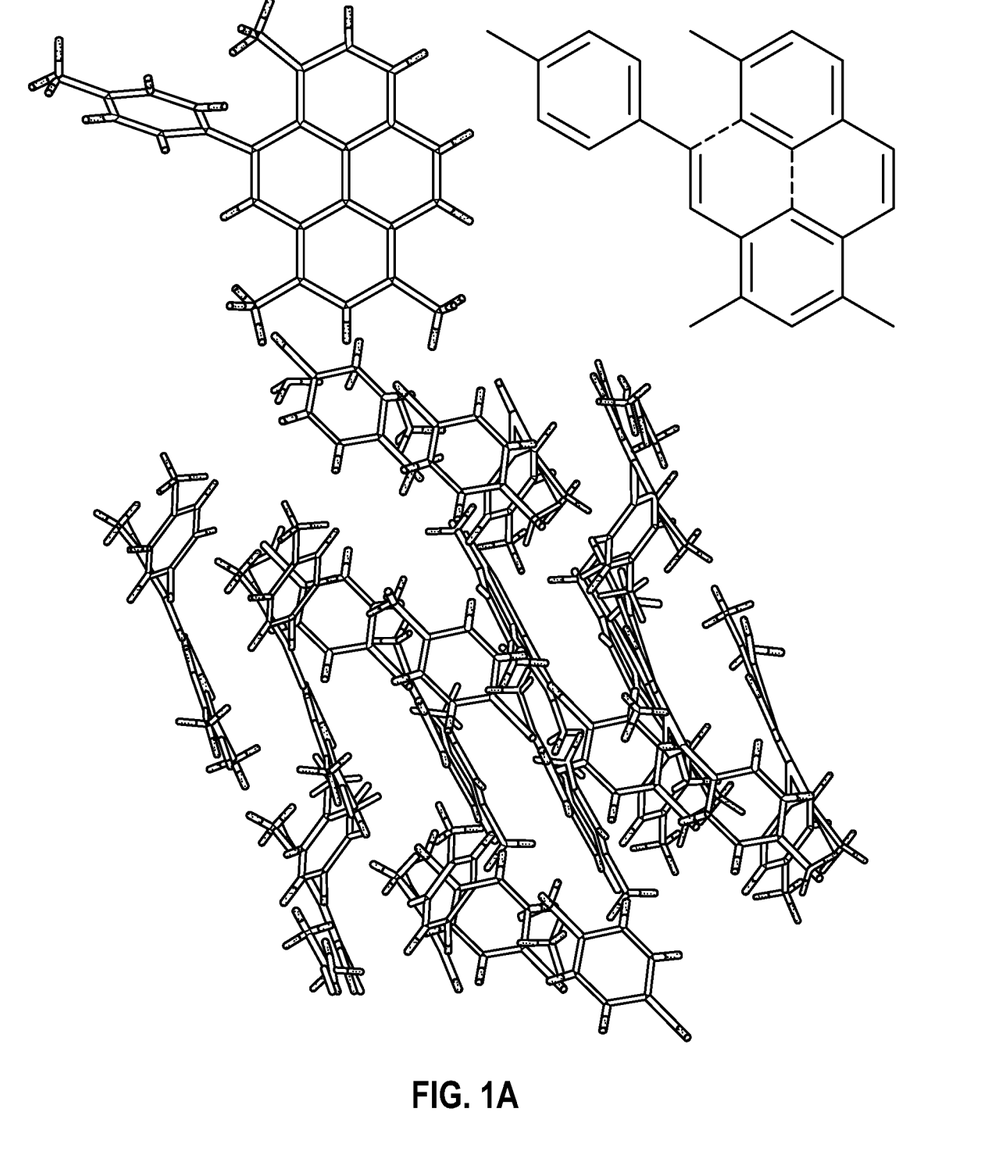
FIG. 1A depicts a single crystal X-ray structure of an embodiment of a compound provided herein, i.e., 1,3,6-trimethyl-5-(p-tolyl)pyrene.
Figure 1B:
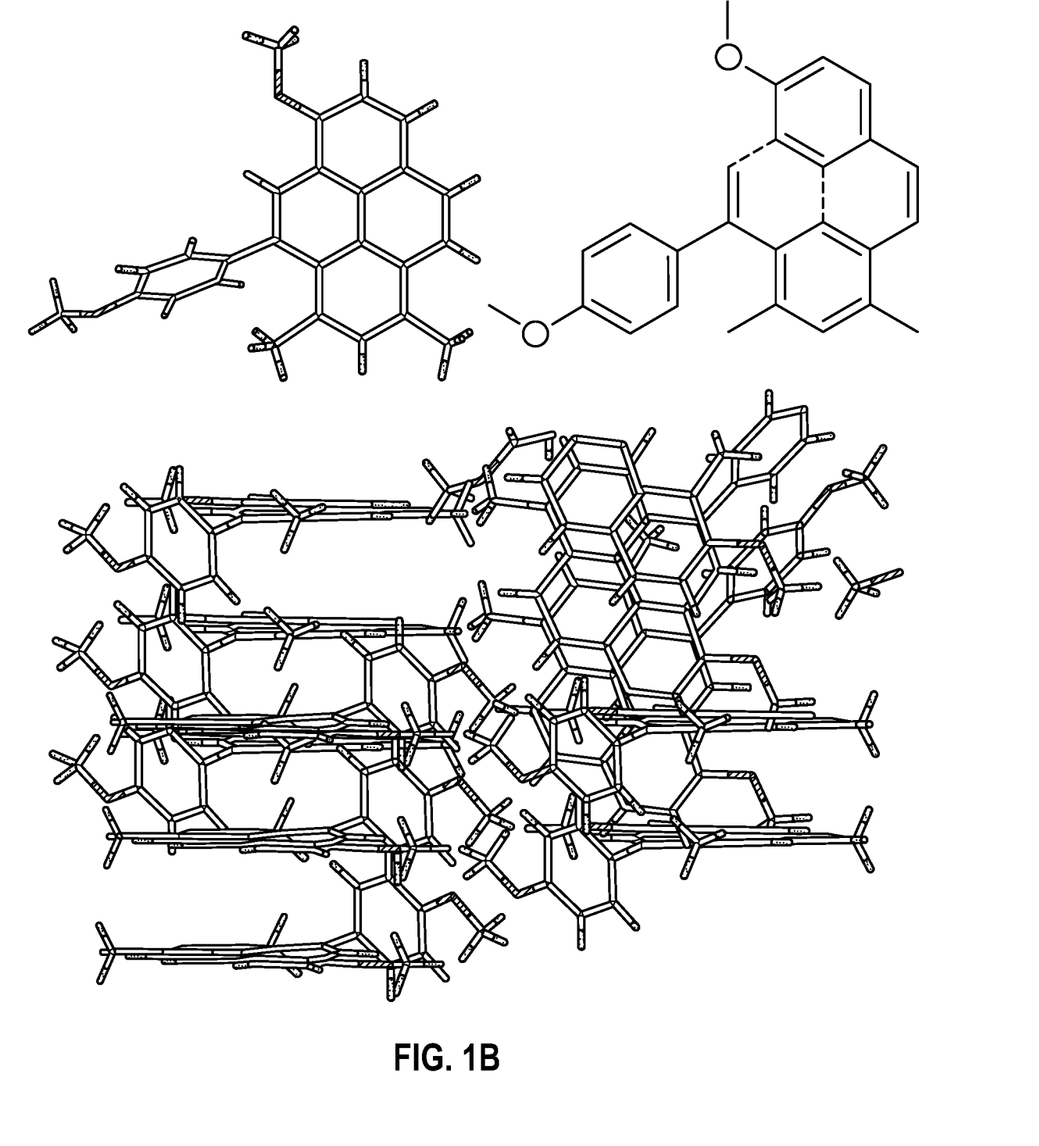
FIG. 1B depicts a single crystal X-ray structure of an embodiment of a compound provided herein, i.e., 6-methoxy-4-(4-methoxyphenyl)-1,3-dimethylpyrene.
Figure 1C:
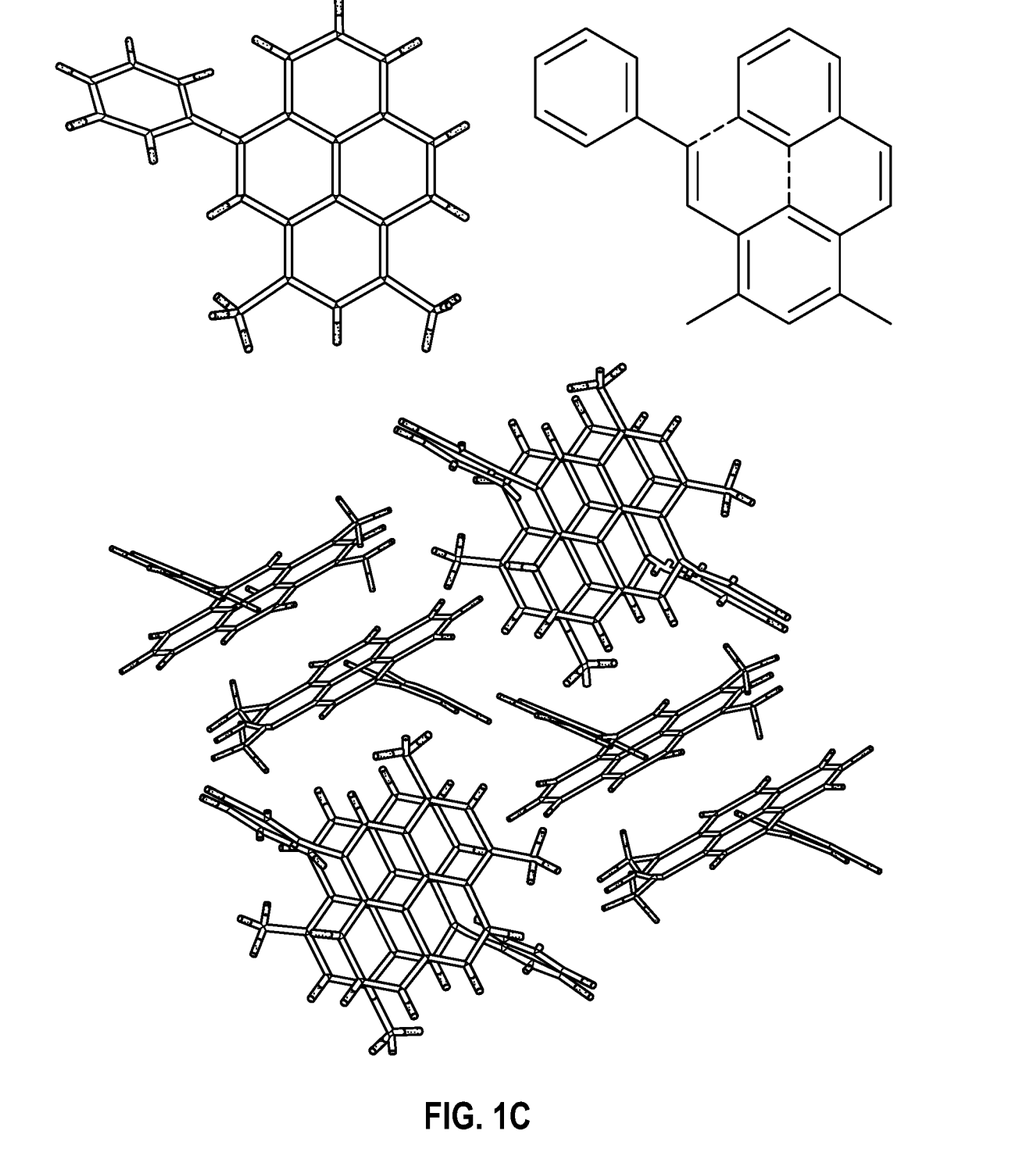
FIG. 1C depicts a single crystal X-ray structure of an embodiment of a compound provided herein, i.e., 1,3-dimethyl-5-phenylpyrene.
Figure 1D:
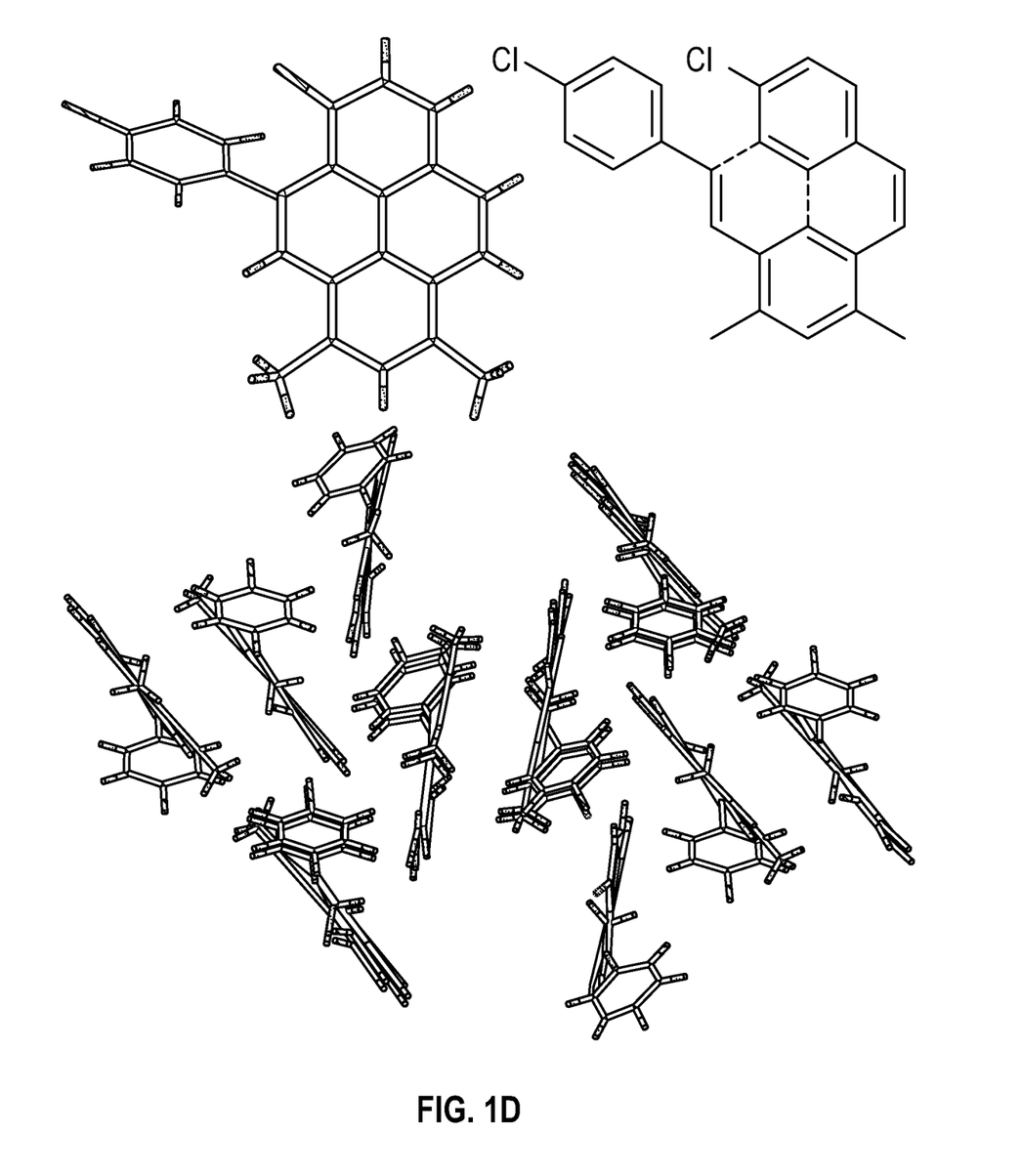
FIG. 1D depicts a single crystal X-ray structure of an embodiment of a compound provided herein, i.e., 6-chloro-5-(4-chlorophenyl)-1,3-dimethylpyrene.

For both cases, the structure of the new products was determined unambiguously by single crystal X-ray analysis (FIG. 1A, FIG. 1B). The synthesis of a product containing only three substituents (FIG. 1C) as well as a product containing an electron withdrawing Cl substituent (FIG. 1D) were also synthesized and its structures were unambiguously determined through X-ray crystallography.

The invention claimed is:

1. A method of forming an arene, the method comprising:
providing a compound of formula (Ia), a compound of formula (Ib), or a combination thereof— formula (Ia)

formula (Ib)

wherein each R is independently selected from the group consisting of a $C_1$-$C_{20}$ alkyl and a $C_1$-$C_{20}$ aryl, and each R' is independently selected from the group consisting of hydrogen, a $C_1$-$C_{20}$ alkyl, a $C_1$-$C_{20}$ aryl, a $C_1$-$C_{20}$ alkoxy, and a $C_1$-$C_{20}$ aryloxy;

irradiating the compound of formula (Ia), the compound of formula (Ib), or the combination thereof to form a compound of formula (II)— formula (II)

irradiating the compound of formula (II) to form a compound of formula (IIIa), a compound of formula (IIIb), or a combination thereof— formula (IIIa)

formula (IIIb)

2. The method of claim 1, wherein the providing of the compound of formula (Ia), the compound of formula (Ib), or the combination thereof comprises:
providing a compound of formula (A)— formula (A)

wherein X is a halogen;
providing a compound of formula (B)— formula (B)

and
contacting the compound of formula (A) and the compound of formula (B) to form the compound of formula (Ia), the compound of formula (Ib), of a combination thereof.

3. The method of claim 2, wherein X is bromine.

4. The method of claim 2, wherein the contacting of the compound of formula (A) and the compound of formula (B) occurs in the presence of a base and a palladium catalyst.

5. The method of claim 1, wherein each R is independently selected from a $C_1$-$C_5$ alkyl.

6. The method of claim 5, wherein each R is methyl.

7. The method of claim 1, wherein each R' is independently selected from a $C_1$-$C_5$ alkoxy.

8. The method of claim 7, wherein each R' is methoxy.

9. The method of claim 1, wherein—
(i) the irradiating of the compound of formula (Ia), the compound of formula (Ib), or the combination thereof occurs in the presence of a first oxidant, and/or
(ii) the irradiating of the compound of formula (II) occurs in the presence of a second oxidant.

10. The method of claim 9, wherein the first oxidant, the second oxidant, or both the first oxidant and the second oxidant comprises iodine.

11. The method of claim 1, wherein each R' is independently selected from a $C_1$-$C_{20}$ alkyl, and the irradiating of the compound of formula (II) converts at least 90%, by mole, of the compound of formula (II) to the compound of formula (IIIa).

12. The method of claim 11, wherein the irradiating of the compound of formula (II) forms the compound of formula (IIIa), and does not form the compound of formula (IIIb).

13. The method of claim 1, wherein each R' is independently selected from a $C_1$-$C_{20}$ alkoxy, and the irradiating of the compound of formula (II) converts at least 90%, by mole, of the compound of formula (II) to the compound of formula (IIIb).

14. The method of claim 13, wherein the irradiating of the compound of formula (II) forms the compound of formula (IIIb), and does not form the compound of formula (IIIa).

15. The method of claim 13, wherein each R' is methoxy.

16. A compound of formula (IIIa), a compound of formula (IIIb), or a combination thereof:

formula (IIIa)

formula (IIIb)

wherein each R is independently selected from the group consisting of a $C_1$-$C_{20}$ alkyl and a $C_1$-$C_{20}$ aryl, and each R' is independently selected from the group consisting of hydrogen, a $C_1$-$C_{20}$ alkyl, a $C_1$-$C_{20}$ aryl, a $C_1$-$C_{20}$ alkoxy, and a $C_1$-$C_{20}$ aryloxy.

17. The compound of claim 16, wherein each R is independently selected from a $C_1$-$C_5$ alkyl.

18. The compound of claim 17, wherein each R is methyl.

19. The compound of claim 16, wherein each R' is independently selected from a $C_1$-$C_5$ alkoxy.

20. The compound of claim 19, wherein each R' is methoxy.

* * * * *